United States Patent
Smalling

(10) Patent No.: US 8,100,937 B2
(45) Date of Patent: Jan. 24, 2012

(54) PRESSURE ASSIST SYSTEM FOR FACILITATING VASCULAR HEMOSTASIS, AND ASSOCIATED METHOD

(75) Inventor: Ron Smalling, Springfield, MO (US)

(73) Assignee: Smalling Medical Ventures, LLC, Springfield, MO (US)

( * ) Notice: Subject to any disclaimer, the term of this patent is extended or adjusted under 35 U.S.C. 154(b) by 987 days.

(21) Appl. No.: 11/973,688

(22) Filed: Oct. 10, 2007

(65) Prior Publication Data

US 2008/0091232 A1   Apr. 17, 2008

Related U.S. Application Data

(60) Provisional application No. 60/850,578, filed on Oct. 10, 2006.

(51) Int. Cl.
*A61B 17/00* (2006.01)
(52) U.S. Cl. .......... 606/204; 606/201
(58) Field of Classification Search ........ 606/201, 606/202, 203, 204; 248/157–159, 407, 423; 128/95.1, 99.1, 103.1, 106.1, 107.1, 110.1, 128/112.1, 116.1, 121.1, 124.1; 601/72–74, 601/80, 134, 135, 137, 138; 269/143, 249, 269/208, 206, 69; 29/257; 482/44–49, 109, 482/141; D24/133, 142, 171, 169, 200, 211–215
See application file for complete search history.

(56) References Cited

U.S. PATENT DOCUMENTS

| | | | | |
|---|---|---|---|---|
| 1,050,836 A * | 1/1913 | Jones | ............. | 601/135 |
| 1,281,653 A * | 10/1918 | Plummer | ............. | 606/203 |
| 3,228,392 A * | 1/1966 | Speyer | ............. | 601/108 |
| 3,831,592 A * | 8/1974 | Lancellotti | ............. | 601/135 |
| 4,164,216 A * | 8/1979 | Person | ............. | 601/41 |
| 4,836,186 A * | 6/1989 | Scholz | ............. | 128/897 |
| 5,195,510 A * | 3/1993 | Svacina | ............. | 601/135 |
| 5,342,388 A * | 8/1994 | Toller | ............. | 606/201 |
| 5,379,758 A * | 1/1995 | Snyder | ............. | 600/213 |
| 5,433,724 A | 7/1995 | Kawasaki et al. | | |
| D373,197 S * | 8/1996 | Schepper | ............. | D24/214 |
| 5,607,380 A * | 3/1997 | Duty | ............. | 482/141 |
| 5,766,206 A | 6/1998 | Wijkamp et al. | | |
| 5,817,037 A * | 10/1998 | Zurbay | ............. | 601/135 |
| 5,843,005 A * | 12/1998 | Chubinsky | ............. | 601/15 |
| 6,068,646 A * | 5/2000 | Lam | ............. | 606/203 |
| 6,102,876 A * | 8/2000 | Winger | ............. | 601/135 |
| 6,241,696 B1 * | 6/2001 | York | ............. | 601/137 |
| D449,379 S * | 10/2001 | Fuhr | ............. | D24/133 |
| 6,488,614 B1 * | 12/2002 | Chang | ............. | 482/110 |
| 6,663,547 B1 * | 12/2003 | Hughes | ............. | 482/141 |
| D503,232 S * | 3/2005 | Semler et al. | ............. | D24/169 |

(Continued)

*Primary Examiner* — Gary Jackson
*Assistant Examiner* — Erin Colello
(74) *Attorney, Agent, or Firm* — Lathrop & Gage LLP

(57) ABSTRACT

A pressure assist system for facilitating vascular hemostasis includes a support bar and a midbar extending perpendicularly from a middle portion of the support bar, for supporting a user's thumb when the user grasps the midbar. A base extends perpendicularly from a bottom of the support bar, for supporting the user's knuckles when the user grasps the midbar. A foot for pressing against a wound is configured with a bottom surface of the base. The midbar may be adjustable along the support bar, according to user grip preference. In a related method, a hand-held pressure assist system is provided, having a support bar, a midbar and base extending perpendicularly from the support bar, and a foot beneath the base. A use's thumb and knuckles are positioned over the midbar and base, respectively. The foot is placed over a wound and downward pressure is applied until hemostasis is achieved.

20 Claims, 8 Drawing Sheets

U.S. PATENT DOCUMENTS

| | | |
|---|---|---|
| 6,890,344 B2 | 5/2005 | Levinson |
| 7,081,124 B2 * | 7/2006 | Sancoff et al. ............... 606/213 |
| D584,412 S * | 1/2009 | Semler et al. ............... D24/169 |
| 7,621,288 B2 * | 11/2009 | Evans ............................ 135/76 |
| 2002/0133104 A1 * | 9/2002 | Bedgood ...................... 601/134 |
| 2002/0147418 A1 * | 10/2002 | Huang ......................... 601/137 |
| 2003/0009116 A1 * | 1/2003 | Luettgen et al. ............... 601/46 |
| 2003/0028214 A1 * | 2/2003 | Benz et al. ................... 606/201 |
| 2003/0105487 A1 * | 6/2003 | Benz et al. ................... 606/201 |
| 2004/0122469 A1 * | 6/2004 | Akerfeldt et al. ............. 606/201 |
| 2004/0176796 A1 * | 9/2004 | Akerfeldt et al. ............. 606/201 |
| 2005/0125025 A1 * | 6/2005 | Rioux ........................... 606/201 |
| 2005/0215929 A1 * | 9/2005 | Dill .............................. 601/135 |
| 2006/0229662 A1 * | 10/2006 | Finkielsztein et al. ........ 606/201 |
| 2007/0142755 A1 * | 6/2007 | Kleiman ...................... 601/120 |
| 2007/0198052 A1 * | 8/2007 | Ben-David ................... 606/201 |
| 2007/0270727 A1 * | 11/2007 | Khorassani Zadeh ........ 601/120 |
| 2008/0139981 A1 * | 6/2008 | Walquist et al. ............. 601/134 |

* cited by examiner

PRESSURE ASSIST SYSTEM FOR FACILITATING VASCULAR HEMOSTASIS, AND ASSOCIATED METHOD

RELATED APPLICATIONS

This application claims priority to U.S. Provisional Patent Application Ser. No. 60/850,578, filed Oct. 10, 2006 and incorporated herein by reference.

BACKGROUND

Achieving hemostasis may be critical to the success of an invasive vascular procedure, such as a diagnostic or therapeutic procedure involving an introduced sheath. In the past, hemostasis has been achieved by manually applying pressure. For example, following cardiac catheterization, a practitioner would press a hand or fingertips to a patient's groin, over an arteriotomy site in the femoral artery. Pressure to the skin would be manually maintained for a period of time (sometimes up to 45 minutes) sufficient to allow the arterial wall to recoil and prevent bleeding from the arteriotomy site.

Advances in arterial compression include hemostatic pressure belts, such as that described in U.S. Pat. No. 5,433,724. The compressive belt detailed therein is positioned around a patient, with a fluid reservoir pouch over an arterial puncture site. Fluid is then pumped into the pouch to increase pressure at the puncture site, under governance of a pressure gauge.

Further advances in hemostasis include suture-mediated closure, along with various resorbable and non-resorbable closure devices such as collagen plugs, gelatin sponges and oxidized cellulose, and cotton, rayon and muslin-based hemostats (respectively). For example. U.S. Pat. No. 5,766,206 provides a penetration member that is inserted through an opening in the skin and an underlying vessel. As the penetration member is withdrawn from the vessel, a pressure gauge indicates when the distal tip of the penetration member has exited the puncture. A hemostatic pharmacon (e.g., collagen) is then ejected from a reservoir within the device, at the puncture site.

Hemostasis may also be aided by hemostatic agents applied to gauze or other wound dressings. U.S. Pat. No. 6,890,344 describes a closure pad for inducing hemostasis through a combination of pressure and the attraction of negatively-charged blood cells to the puncture site, by means of a cationic substance on the pad.

Although the aforementioned closure devices have generally reduced the time needed to achieve hemostasis, devices such as the hemostatic belt may be difficult to secure to a patient, and may slip from the desired compression site if not carefully applied. Further, such a "hands free" device may inspire false confidence in a busy practitioner, who may be tempted to keep lesser watch on a patient using a belt. All of these factors may result in increased bleeding from an arteriotomy site.

Complications have also arisen due to use of resorbable and non-resorbable hemostatic agents such as the ejected pharmacon. For example, allergic reaction, hematomas, arterio-venous fistula, infection, device deployment failure and pseudoanuerysms have been observed, and both resorbable and nonresorbable hemostatic agents have additionally been reported to cause symptomatic mass lesions, most commonly following intra-abdominal surgery. These masses, e.g., textilomas, may be detected in tomographic and other imaging procedures and mistaken for recurrent tumor. Such complications are sufficiently present that manufacturers of several such agents, e.g., Surgigel and Gelfoam, recommend removal of the material once hemostasis is achieved. Ribalta, T., "Textiloma (Gossypiboma) Mimicking Recurrent Intracranial Tumor," *Archives of Pathology & Laboratory Medicine*, July 2004. In addition, resorbable and non-resorbable hemostatic agents are expensive, increasing the cost of invasive vascular procedures to hospitals or clinics and to patients.

Accordingly, in the majority of patients, groin closure is still achieved by manual sheath removal and application of hand or fingertip pressure to the groin area. Gauze and wound dressings impregnated with hemostatic agents may shorten the time period necessary to achieve hemostasis by manual compression; however, manual compression still requires time and effort on behalf of vascular suite personnel, who must learn and carry out effective hemostasis techniques. A practitioner applying manual compression is additionally subject to hand fatigue, especially in complicated cases requiring a greater compression time.

SUMMARY

The pressure assist system and related method disclosed herein facilitate manual compression hemostasis and may overcome the problems associated with prior art devices.

In one embodiment, a pressure assist system for facilitating vascular hemostasis includes a support bar and a midbar extending perpendicularly from a middle portion of the support bar, for supporting a user's thumb when the user grasps the midbar. A base extending perpendicularly from a bottom portion of the support bar supports the user's knuckles when the user grasps the midbar. A foot is configured with a bottom surface of the base, for pressing against a wound.

In one embodiment, a pressure assist system for facilitating vascular hemostasis has a support bar for supporting a user's arm or wrist and an adjustable midbar for supporting a user's thumb when the user grips the midbar with the thumb. The midbar extends perpendicularly from the support bar when connected with the support bar at one of a plurality of user-selectable connection points. A base formed with a bottom portion of the support bar extends perpendicularly from the support bar, for supporting the user's knuckles when the user grips the midbar with the thumb. A foot, for pressing against a wound, connects with a bottom surface of the base.

In one embodiment, a pressure assist system for facilitating manual hemostasis of a wound includes a hand-held hemostatic assist device with a vertically-oriented support bar, a midbar and a base. The support bar supports a medial or lateral surface of a user's wrist. The midbar supports the user's hand when the user grips the midbar. The midbar connects with the support bar at one of a plurality of user-selectable connection points, and extends horizontally from the support bar when connected. The base is a horizontally-oriented base extending from a bottom portion of the support bar, for transferring pressure applied by the user from the hemostatic assist device to the wound.

In one embodiment, a method for facilitating vascular hemostasis includes providing a hand-held pressure assist system, the system having: a support bar, a midbar extending perpendicularly from a center portion of the support bar, a base extending perpendicularly from a bottom portion of the support bar, and a foot beneath the base. The thumb is positioned over the midbar and the knuckles are positioned on the base. The system is positioned over a wound such that the foot covers the wound, and downward pressure is applied to the midbar and the base with the thumb and the knuckles, until hemostasis is achieved.

In one embodiment, a pressure assist system for facilitating vascular hemostasis has a support bar for supporting a user's arm or wrist along a medial or lateral surface. The support bar has a plurality of connection points for accepting an adjustable midbar. A base extending perpendicularly from a bottom portion of the support bar transfers pressure from a user's knuckles to a wound. The base supports the user's knuckles when the medial or lateral arm or wrist surface contacts the support bar. A disposable foot for contacting the wound removably attaches with the base.

DETAILED DESCRIPTION

Before proceeding with the detailed description, it is to be appreciated that the present teaching is by way of example, not limitation. The illustrations herein are not limited to use or application with a specific type of pressure assist system or method. Thus, although the instrumentalities described herein are for the convenience of explanation, shown and described with respect to exemplary embodiments, it will be appreciated that the principals herein may be equally applied in other embodiments of pressure assist systems and methods.

Figure 1:
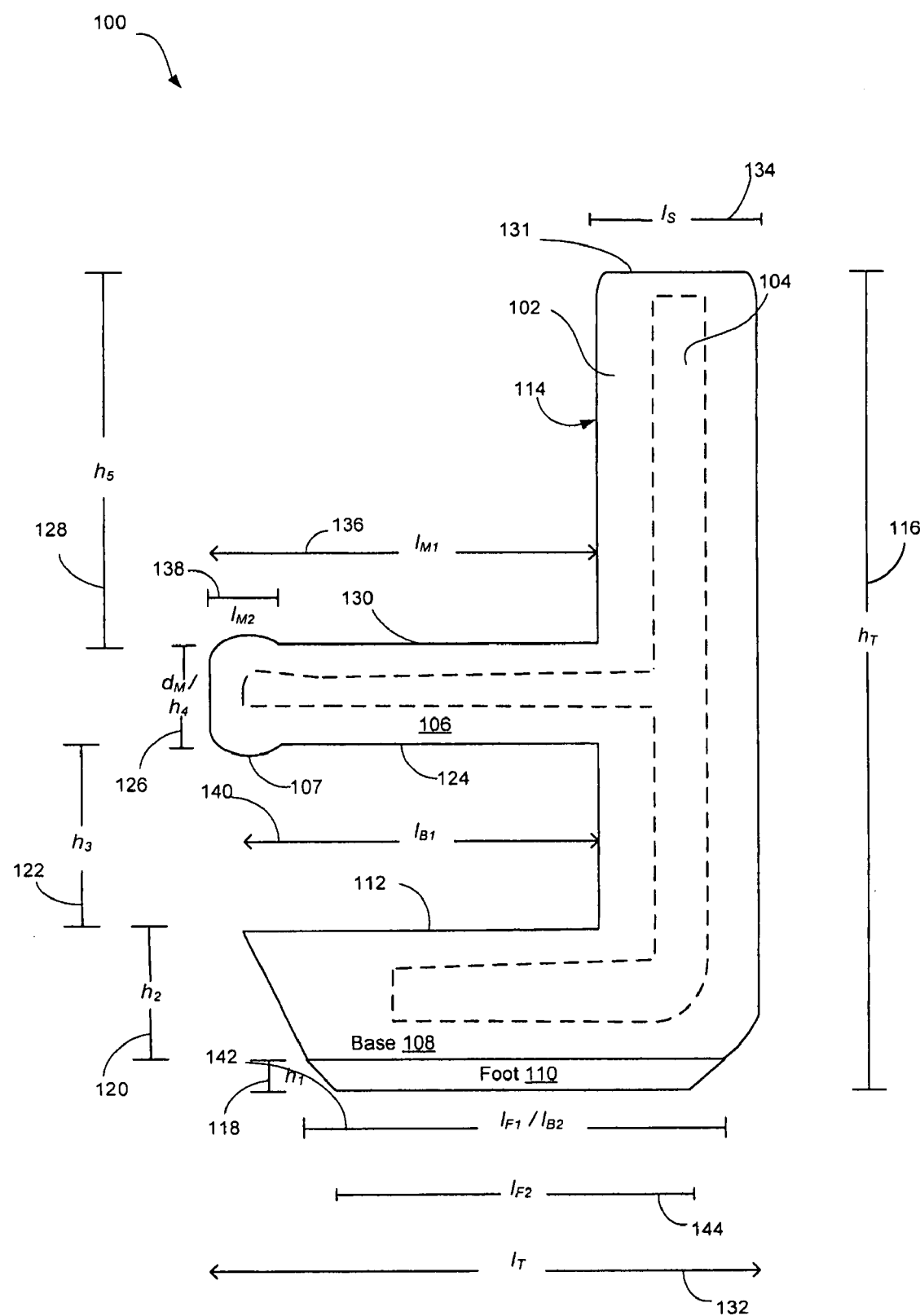
FIG. 1 is a schematic side view of a pressure assist system for facilitating vascular hemostasis, illustrating exemplary dimensions.

FIG. 1 is a side view of a hand-held pressure assist system 100, for facilitating vascular hemostasis. For ease of discussion, system 100 is described herein below with respect to hemostasis of a femoral artery puncture site; however, those skilled in the art will recognize that system 100 may be equally applied for enhanced hemostasis at other vessels in the circulatory system. For example, system 100 may provide enhanced hemostasis at any site where manual compression is generally used—for example, at radial or brachial arteriotomy or cannulation sites.

System 100 includes a support bar 102 with an inner support 104, a mid-bar 106 and a base 108, both extending perpendicularly from support bar 102. Base 108 overlies a foot 110. Inner support 104 (illustrated by a dotted line in FIG. 1) is formed of a structurally supportive and strong material such as metal or hard plastic. Support 104 is for example a rigid metal plate or post that provides structure and strength to system 104. Support 104 may be covered by a plastic laminate or a rubber or plastic support bar 102 that is softer than support 104, to provide a comfortable fit and, if desired, a degree of conformity to a practitioner's hand, wrist and forearm. System 100 is reusable and easy to clean, composed for example of materials that may be sterilized in an autoclave. In one embodiment, support bar 102, mid-bar 106, base 108 and optionally, foot 110 are formed as a unitary body of rubber, plastic or polymer around inner support 104. In one embodiment, foot 110 is removable from base 108. Foot 110 may be removed from base 108 for cleaning between uses, or foot 110 may be a disposable foot that is removed from base 108 and discarded after use.

In one embodiment, foot 110 is placed atop a wound such as a venous puncture site or an arteriotomy site (e.g., a puncture into the femoral artery), with support bar 102 in a relatively vertical position. A practitioner rests the knuckles of his/her fingers upon a substantially horizontal top 112 of base 108 and loops the thumb over midbar 106, also relatively horizontal, for example with the wrist braced against a front surface 114 of the vertically oriented support bar 102. Midbar bulb 107 is slightly larger than midbar 106, to present the practitioner's thumb from sliding off the end of midbar 106.

Pressure may be applied to the puncture site and surrounding skin by pressing the knuckles downward against top 112. System 100 for example allows for four knuckle-points of contact along top 112, in addition to downward force provided by the practitioner's thumb pressing midbar 106, to generate even application of pressure along foot 110. In addition, system 100 may harness gravity and the weight of the arm for enhanced pressure application. A practitioner for example stands next to a prone patient so that the weight of his/her arm contributes to the total downward pressure applied where foot 110 meets the arterial puncture site and surrounding skin. Utilizing system 100 in this manner, the practitioner may evenly administer a larger total pressure over a larger area than is generally addressed by using the fingertips, while also enjoying a position that is more ergonomically friendly than application of pressure from the fingertips, which are more easily fatigued than the knuckles.

System 100 may be produced in a range of sizes, for comfortable fit with a range of user grips (e.g., small, medium and large hand sizes). In one embodiment, system 100 has a total height ($h_T$) 116 of about 8 inches, including first, second, third, fourth and fifth heights $h_1$-$h_5$. First height ($h_1$) 118, represents the height of foot 110, about ½ inch. Second height ($h_2$) 120 corresponds to the height of base 108, which is for example about 1 inch. Third height ($h_3$) 122 of about 1½ to 2 inches represents the distance from top 112 of base 108 to a bottom surface 124 of midbar 106. Fourth height ($h_4$) 126 corresponds to the height of midbar 106. Midbar 106 may be elliptical (e.g., circular or cylindrical) in cross-section, to comfortably accommodate the natural curve at the web of skin between the inner thumb and the palm. Fourth height 126 may therefore equal a diameter ($d_M$) of midbar 106. Hereinafter, $h_4$ 126 and $d_M$ 126 may be used interchangeably.

To prevent the practitioner's thumb from sliding off an end of midbar 106, midbar bulb 107 may have a diameter ($d_B$) 127 (see FIG. 2) that exceeds $d_M$ 126. Diameter $d_M$ 126 is for example 1⅛ inches, and diameter $d_B$ 127 is for example 1⅝ inches. Diameter $d_B$ 127 may therefore slightly overlap $h_4$ 126 and fifth height ($h_5$) 128. Fifth height $h_5$ 128 represents the height from a top surface 130 of midbar 106 to the top 131 of system 100, for example 3½ to 4 inches.

System 100 for example has a total length ($l_T$) 132 of 4-5 inches, with support bar 102 having a support bar length ($l_S$) 134 of about ¾ to 1½ inches. Midbar 106 may be about 3¾ inches long, including midbar length ($l_{M1}$) 136, about 3¼ inches, and a bulb length ($l_{M2}$) 138 of about ½ inch. Top 112 of base 108 for example has a top or first base length ($l_{B1}$) 140 of 3¼ inches, tapering to a second, or bottom base length ($l_{B2}$) 142 of about 3 inches. As shown in FIG. 1, system 100 may be contoured such that base 108 is approximately equal in length to foot 110, where the two meet. Thus, $l_{B2}$ 142 may also be referred to as a top, or first foot length $l_{F1}$ 142. Foot 110 for example tapers from $l_{F1}$ 142, which is about 3 inches, to a second, bottom foot length $l_{F2}$ 144 of about 2 inches. However, it will be appreciated that lengths $l_{F1}/l_{B2}$ and $l_{F1}$ may vary as a matter of design preference or desired function, as may other dimensions described above, and with respect to FIGS. 2-7F, below.

Figure 2:
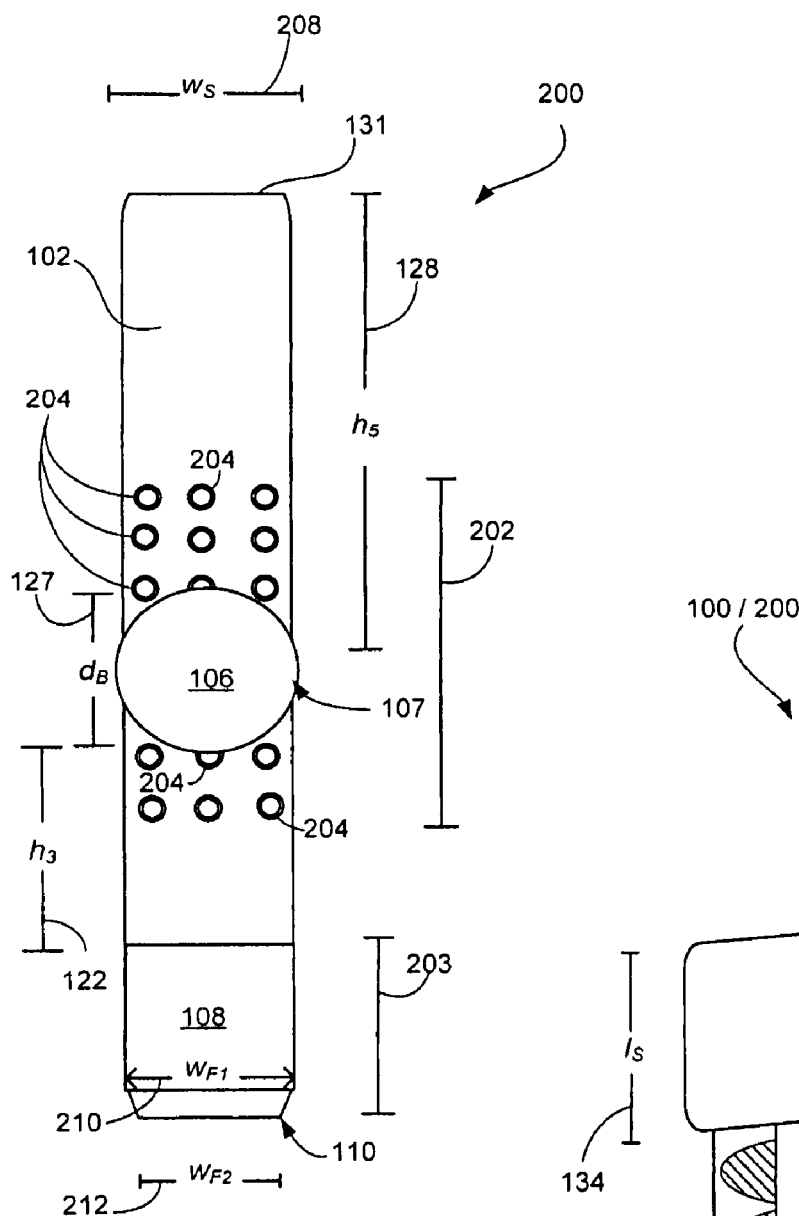
FIG. 2 is a schematic front view of an adjustable pressure assist system.

In one embodiment, the disclosed pressure assist system provides variable sizing. Pressure assist system 200, FIG. 2, shares features of system 100, which are numbered as in FIG. 1. As shown in FIG. 2, system 200 includes a user-adjustable midbar 106 that that may be placed at a variety of positions over a middle portion 202 of support bar 102, to accommodate a range of user hand sizes. System 200 is for example configured with a peg-and-hole, screw-in-place or otherwise adjustable midbar and support bar, such that third height $h_3$ 122 is adjustable according to user preference, hand size, application and/or comfort. In one embodiment, support bar 102 includes a plurality of connection points, or holes, 204 into which one or more pegs 206 (see FIG. 4A) fit. Pegs 206 fit with or are formed with midbar 106. Pegs 206 may be screws sized to fit holes 204, such that midbar 106 may be twisted or screwed into and out of place. Alternately, holes 204 and corresponding pegs 206 may be configured with lock and key features, for example, a hole 204 may include an l-shaped channel to accommodate a raised feature on a peg 206, so that the peg may be advanced forward into the hole and then twisted, to lock the peg into position. Holes 204 may be aligned in horizontal and vertical rows, as shown in FIG. 2, to provide a range of midbar 106 placements and to accommodate a range of hand positions. Likewise, midbar 106 may be raised sufficiently above base 108 that a user's knuckles do not contact base 108, for example to provide an effective hemostatic aid to a practitioner with injured knuckles. Base 108 extends from a bottom portion 203 of support bar 102.

Figures 4A, 4B:
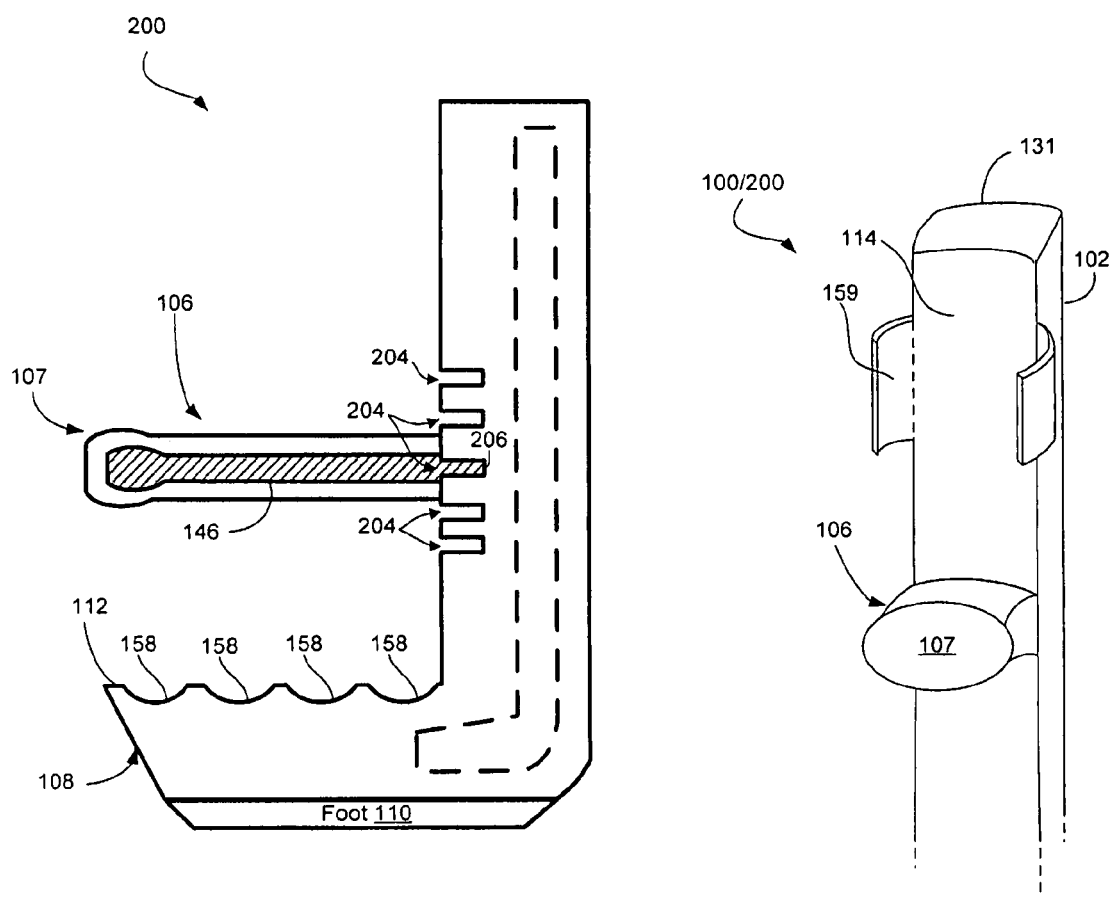
FIG. 4A is a schematic side view of the pressure assist system of FIG. 2.
FIG. 4B is a schematic partial front perspective view of the pressure assist system of FIGS. 2, 3 and 4A, with a wrist or forearm brace.

A peg or pegs 206 may be formed as extensions of an adjustable, homogeneous midbar .106. Alternately, peg or pegs 206 may be formed as an extension of, or attached to, a midbar support 146 (see FIG. 4A), which is for example metal or another structurally strong material embedded in a rubber or plastic midbar 106. Rounded holes 204 are shown in FIG. 2 and squared holes and pegs 204, 206 are shown in FIG. 4, for ease of illustration. However, it will be appreciated that holes 204 and pegs 206 may take other geometric shapes and/or include threading and/or the above mentioned lock-and-key features without departing from the scope hereof. Support bar 102 and base 108 are for example a unitary piece or body of hard rubber, plastic or composite material with holes 204 for accepting one or more pegs 206 disposed with midbar 106. Optionally, a softer material with a rigid, j-shaped inner support (see FIG. 7E) forms support bar 102 and base 108, with holes 204 disposed through one or both of the support bar and the inner support, for accepting pegs 204 of adjustable midbar 106.

System 200 has a consistent support bar width ($w_S$) 208, of about 1¼ to 1½ inches, corresponding to a first foot width ($w_{F1}$) 210 at the joinder of base 108 and foot 110. Foot 110 tapers to a second foot width ($w_{F2}$) 212, for example about 1 inch.

Figure 3:
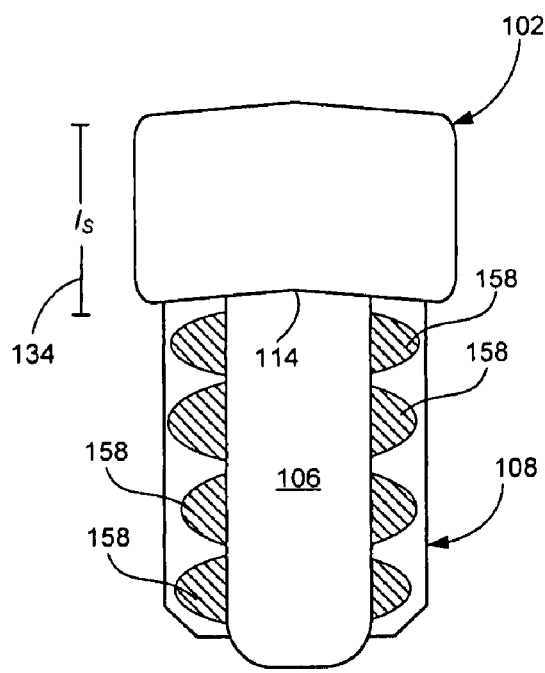
FIG. 3 is a schematic top view of the system of FIG. 1 or FIG. 2.

As shown in FIG. 3, front surface 114 of system 100/200 may be slightly concave or inwardly-angled, to accommodate the curvature of a user's wrist and/or forearm. Also as shown in FIG. 3, top 112 of base 108 may be formed with depressions 158 for accommodating a practitioner's knuckles. The side view of system 200 shown in FIG. 4A further illustrates depressions 158. As shown in FIG. 4A, for increased comfort, even distribution of pressure or as a matter of design preference, top 112 may be formed with depressions 158 for accommodating the knuckles. Top 112 may alternately be curved to accommodate the varying heights of the knuckles. Padding (see FIG. 5) such as detachable foam may also be incorporated into one or both of top 112 and mid-bar 106, as well as along front surface 114 of support bar 102, as a matter of user preference.

An additional curved brace 159, shown in the partial front view of FIG. 4B, may be formed with or attached to support bar 102 of system 100/200 above midbar 106, to provide additional support to and/or prevent excessive movement of the practitioner's wrist or forearm while grasping system 100/200. As noted, systems 100, 200 may be composed entirely of materials that may be sterilized in an autoclave. However, systems 100, 200 may also be made of disposable materials or include disposable components that may be discarded after use.

Figure 5:
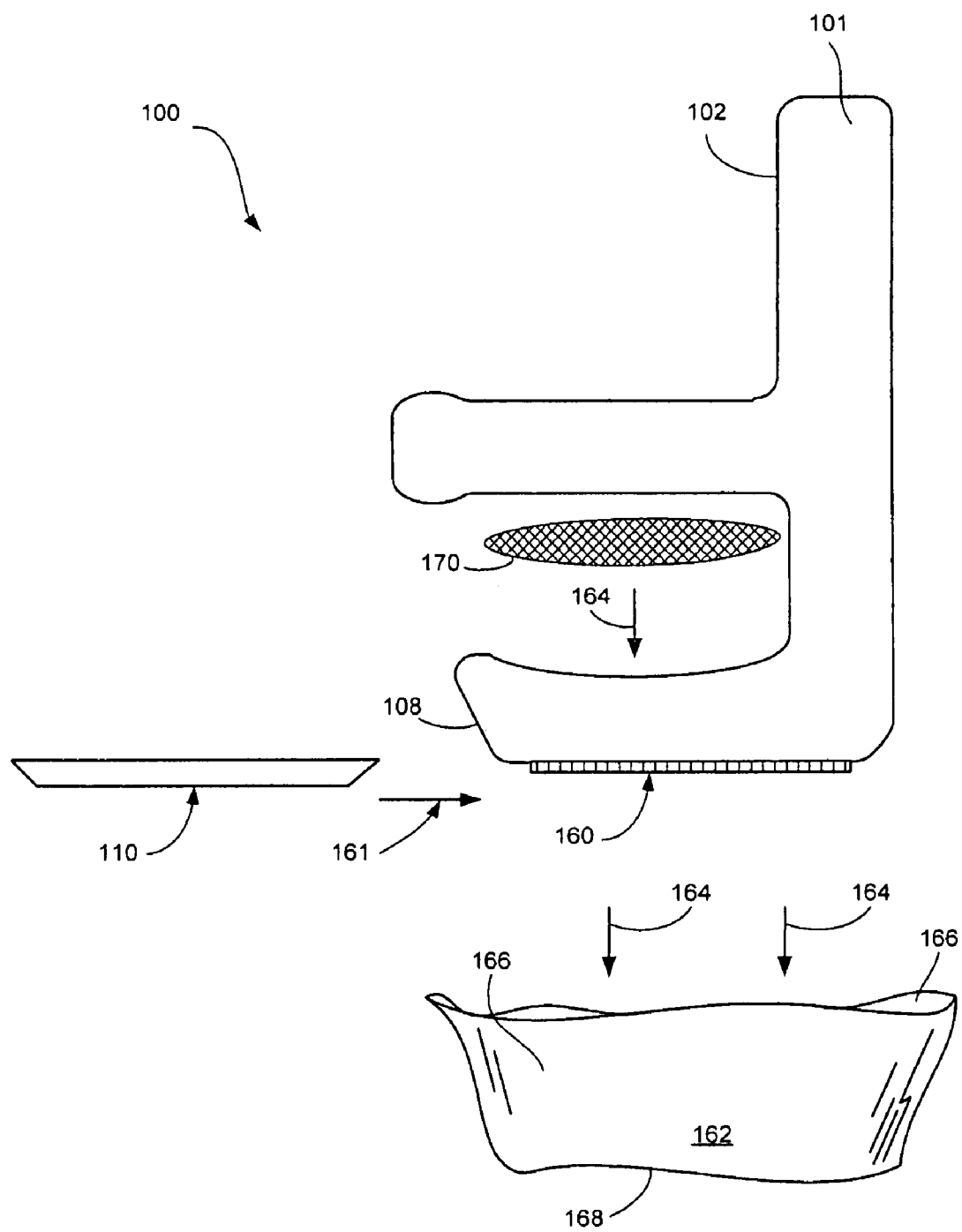
FIG. 5 is a schematic side view of the system of FIG. 1, illustrating a removable foot and a disposable covering.

As shown in FIG. 5, system 100/200, support bar 102, midbar 106 and base 108 may be formed as a unitary pressure assist device 101. A removable foot 110 connects to base 108 via a fastener, for example via one or more inner foot grooves (not shown) that slide along a rail 160, in the direction of arrow 161, to connect with base 108. Alternately, foot 110 may be a disposable pad (e.g., sterile gauze, untreated or treated with a hemostatic agent and/or an analgesic or anesthetic) that attaches to base 108 via a hook-and-loop fastening system such as a hook and loop system (e.g., Velcro®), or via a single-use or reusable adhesive. The adhesive (not shown) may be covered with a non-stick strip to protect the adhesive prior to use. A sterile disposable covering 162 may alternately or optionally be used to cover foot 110, and also base 108, if desired. System 100/200 is for example placed or pressed into covering 162 as indicated by arrows 164, and covering 162 is attached to foot 110 (and optionally base 108) by Velcro, adhesive, shrink-fit or other known fasteners. It will be understood that alternately, covering 162 may be placed or pressed onto foot 110 (and optionally base 108). Where a hook-and-loop fastening system is used, fasteners (not shown) may be disposed with sides 166 rather than base 168 of covering 162, to insure a comfortably smooth surface where system 100/200 contacts a patient's skin.

Also as shown in FIG. 5, padding 170 may cushion top 112 of base 108, for a comfortable fit with a practitioner's knuckles. Padding 170 may be formed with or permanently attached to top 112, or, as shown, padding 170 may be removably attached to top 112. In one embodiment, padding 170 is a pad of memory foam that forms to a practitioner's knuckles. In another embodiment, padding 170 is a gel pad. Padding 170 may also be gauze, soft plastic or another suitably soft material for cushioning the knuckles. Padding 170 may be disposable or formed with materials that can be autoclaved or otherwise sterilized between uses, as necessary.

Figure 6:
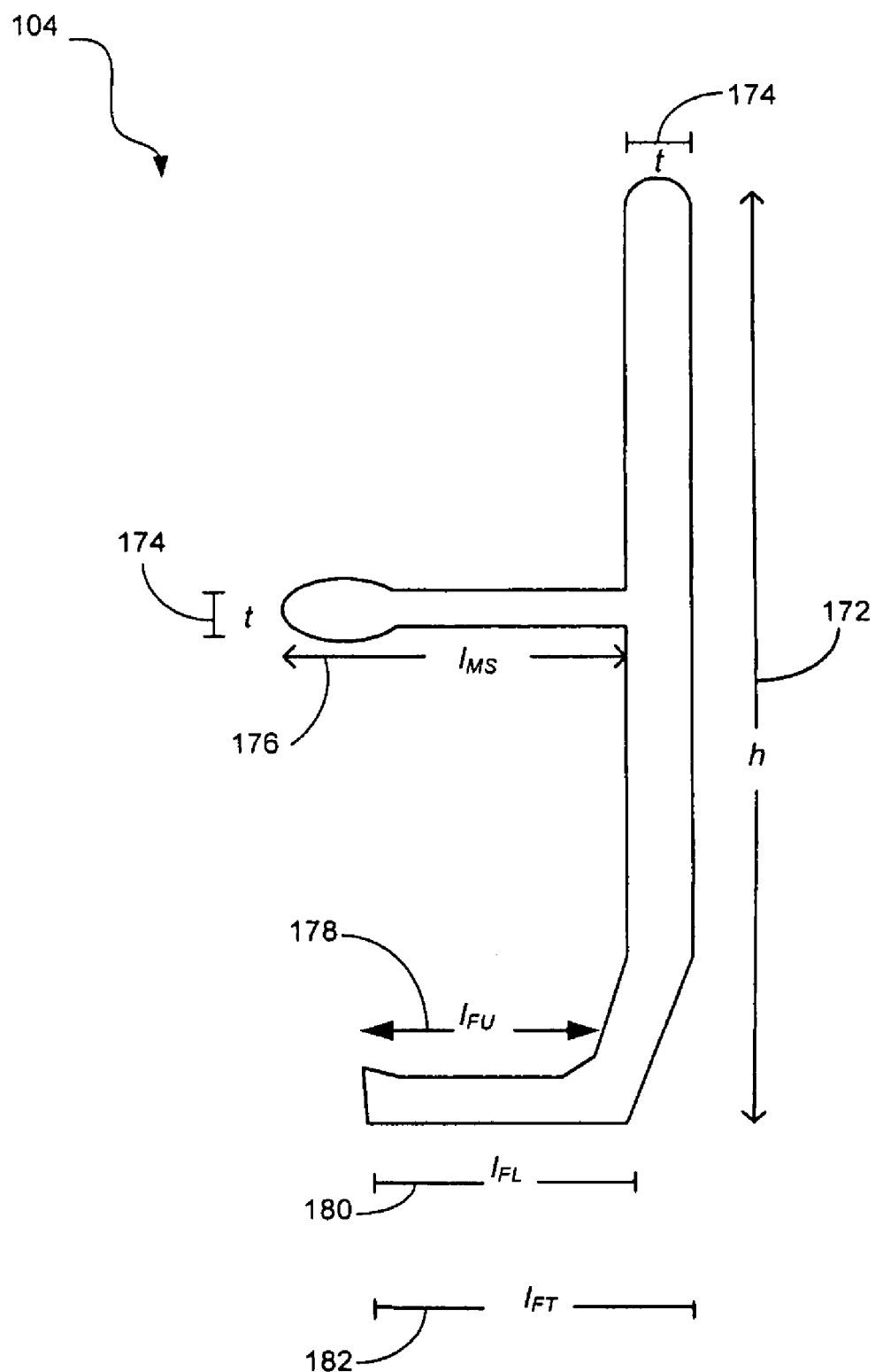
FIG. 6 schematically depicts an inner support of the system of FIG. 1.

FIG. 6 illustrates exemplary dimensions of inner support 104 of systems 100, 200. Support 104 has a height (h) 172 of about 6 to about 8 inches, a thickness (t) 174 ranging from about ¾ inch to about 1 inch (not to scale) over support 104, a midbar support length ($l_{MS}$) 176 of about 3¾ to 2 inches, a top/upper foot length ($l_{FU}$) 178 of about 2¾ to 3 inches, a bottom/lower foot length ($l_{FL}$) 180 of about 3 inches (e.g., 2¹⁵⁄₁₆ inches) and a total foot length ($l_{FT}$) 182 of about 3¼ to 3½ inches.

Figure 7A:
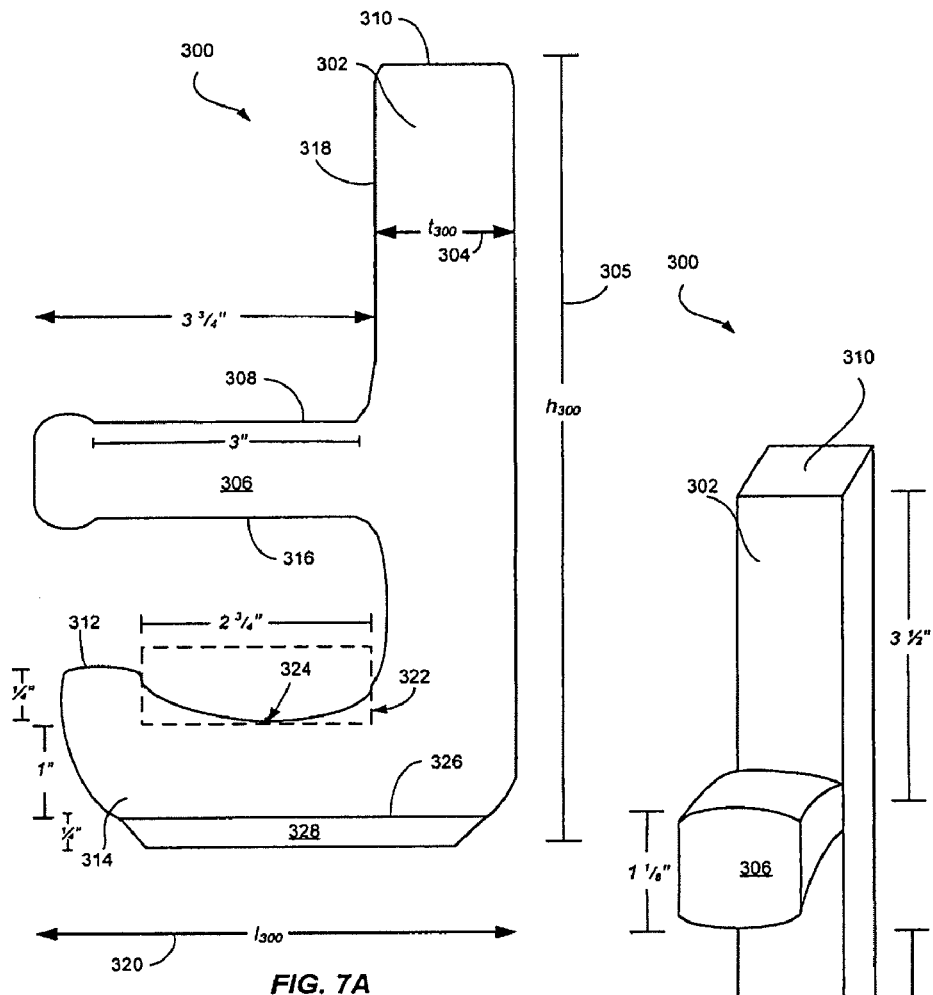
FIG. 7A is a schematic side view of a pressure assist system, having a base with a curved top.
Figure 7B:
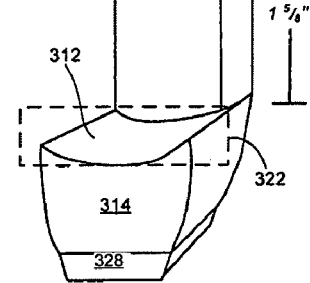
FIG. 7B is a schematic front perspective view of the system of FIG. 7A.

FIGS. 7A-7B show side and front views of a pressure assist system 300 for enhanced vascular hemostasis, with exemplary dimensions (not drawn to scale). System 300 includes a rubber or plastic body 302 having a thickness ($t_{300}$) 304 of about ¾ inch, and a height ($h_{300}$) 305 of about 7½ inches. In one embodiment, body 302 is a hard polished rubber body having a midbar 306 with an upper face 308 positioned at about 3½ inches from top 310 of system 300, and a top 312 of base 314 positioned about 1⅝ inches below a bottom face 316 of midbar 306. Body 302, midbar 306 and base 314 are for example formed as a continuous rubber or plastic object. Base 314 extends about 3 inches from a front surface 318 of system 300. Midbar 306 is about 1⅛ inches in diameter and extends about 3¾ inches from front surface 318. System 300 has a total length ($l_{300}$) 320 of about 4½ inches. A curved knuckle rest portion 322 (indicated by a dashed box) of base 314 is about 2¾ inches long, and is recessed about ¼ inch from the top 312, at its lowest point 324. Between point 324 and a bottom 326 of base 312, body 302 is about 1 inch thick. A foot 328 extends about ¼ inch from bottom 326.

As shown in FIG. 7B, midbar 306 may be slightly offset from base 314 (e.g., curved or out of alignment with base 314), as a matter of design or comfort preference, to accommodate a range of user gripping positions (e.g., a grip where the thumb is not aligned above the knuckles). Likewise, both offset of midbar 306 and height of midbar 106 ($h_4$ 126) may be adjusted to customize fit of system 300 per a user's grip preference (hand size and/or grip position), via a peg-and-hole system as described above with respect to FIG. 2. Optionally, base 314 may be wider than midbar 306, providing a range over which each individual user may position his or her knuckles, relative to thumb position.

Figure 7C:
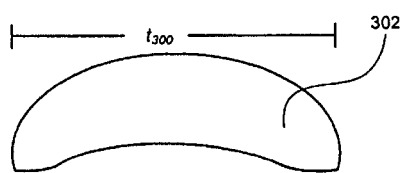
FIG. 7C is a schematic top view of the system of FIG. 7A.
Figure 7D:
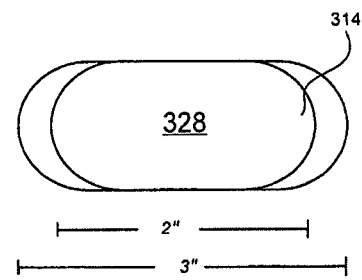
FIG. 7D is a schematic bottom view of the system of FIG. 7A.
Figure 7E:
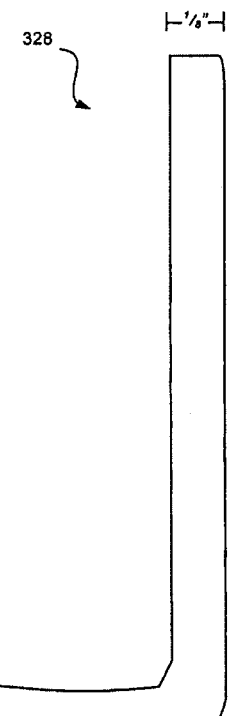
FIG. 7E illustrates an inner support for the system of FIG. 7A.
Figure 7F:
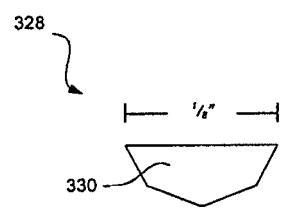
FIG. 7F schematically illustrates a front tip of the inner support of FIG. 7E.

FIG. 7C shows a top, cross-sectional view of body 302 of system 300, taken above (and thus excluding) midbar 306, base 314 and foot 328. FIG. 7D shows a bottom view of base 312 and foot 326, FIG. 7E illustrates a support 330 that is for example embedded in rubber/plastic body 302 to provide strength and durability to system 300. Support 330 is for example a ⅛ inch thick, j-shaped metal or hard plastic plate or post. The absence of a midbar support, as shown in FIGS. 1 and 4-6, may provide increased flexibility to midbar 306, such that thumb pressure on midbar 306 causes slight downward and/or sideways flexion. A slightly flexible midbar 306 may allow for practitioners with a variety of hand sizes to comfortably use system 300, by applying the amount of pressure necessary to bend the midbar to the most comfortable position. FIG. 7F shows a schematic front, cross-sectional view through a front end 330 of support 328, taken along dotted line A, FIG. 7E.

Figure 8:
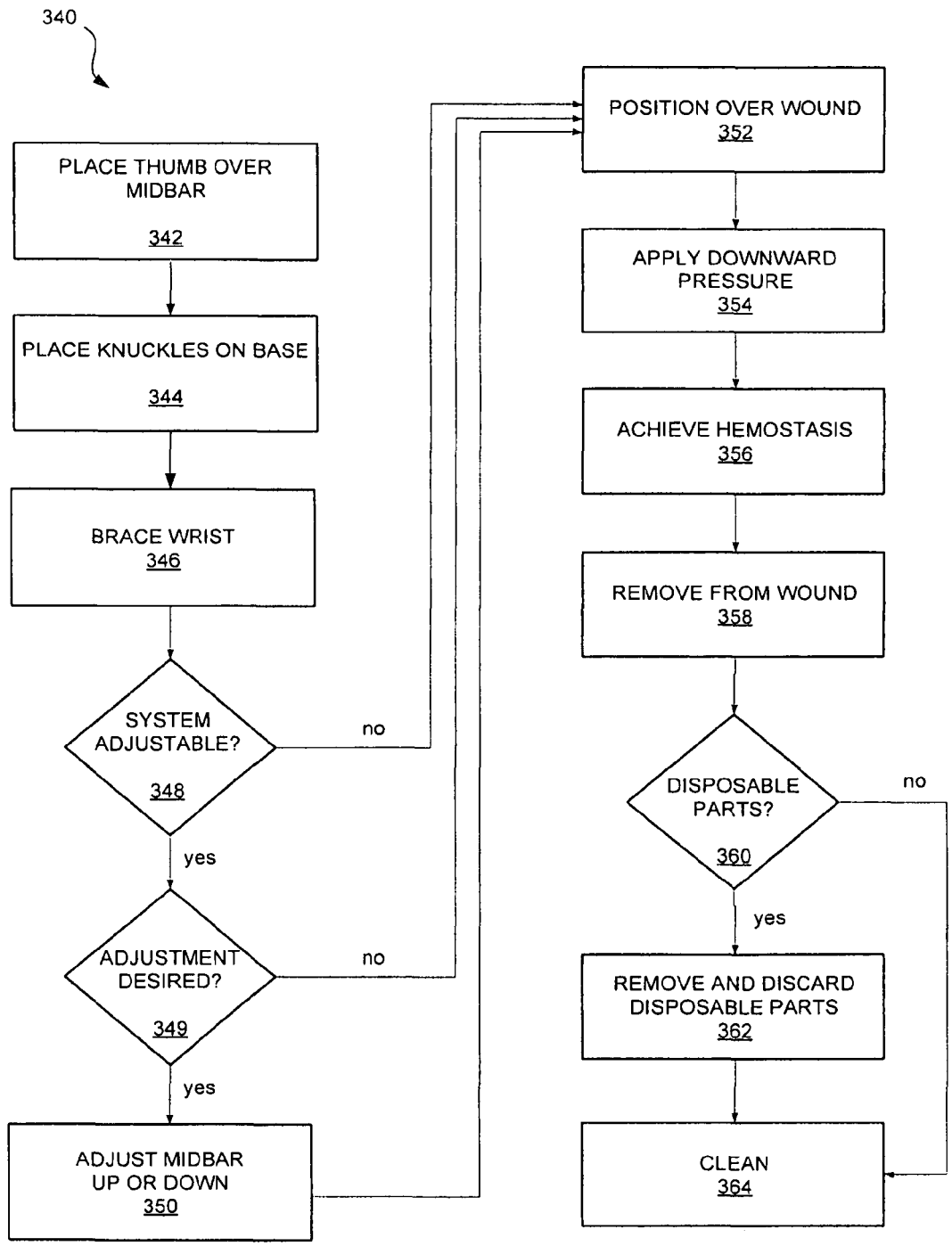
FIG. 8 is a flow chart depicting a method for achieving vascular hemostasis with a pressure assist system, as illustrated in FIGS. 1-7F.

In practice, the above described pressure assist systems may be used to facilitate vascular hemostasis as shown in flow chart 340, FIG. 8. In step 342, a practitioner places the thumb over a midbar, for example with the midbar held snugly against the web of skin between the thumb and the palm. In step 344, the knuckles are placed on a base, for example, upon knuckle rest portion 320, base 312. The practitioner braces his/her wrist against an inside of a support bar or system body, e.g., support bar 102/body 302, in step 346. If the pressure assist system is adjustable, decision 348, and if adjustment is necessary, decision 349, the midbar is adjusted up or down the support bar/body, to fit the practitioner's grip (e.g., preferred grip position or hand size), in step 350. The system is then placed over a wound, for example an arteriotomy site, with a foot of the device covering the wound, in step 352, and the practitioner applies downward pressure upon the base with the knuckles, and upon the midbar with the thumb, in step 354. The system is held in place, and pressure applied, until hemostasis is achieved, step 356. Once hemostasis is confirmed, the pressure assist system is removed from the wound, step 358. If the pressure assist system includes disposable parts, such as a disposable covering for the base or a disposable foot, decision 360, the disposable parts are removed and discarded in step 362, and the pressure assist system cleaned as necessary, in step 364, for example with sanitizing cleaners or in an autoclave, according to applicable hospital, clinic or practitioner standards.

It is to be understood that steps 342-364 need not be performed in the order described herein. For example, a practitioner may choose to position his or her knuckles (step 344) or wrist (step 346) before placing his or her thumb (step 342). Likewise, a practitioner may choose to position the pressure assist system upon the wound (step 352) prior to positioning his or her hand in pressure-holding position. Also, not all of steps 342-364 need necessarily be performed for effective hemostasis.

Changes may be made in the above systems and methods without departing from the scope thereof. For example, features described with respect to one shown or described embodiment of a pressure assist system or method may be incorporated with another shown or described embodiment. It should thus be noted that the matter contained in the above description and/or shown in the accompanying drawings should be interpreted as illustrative and not in a limiting sense. The following claims are intended to cover generic and specific features described herein, as well as all statements of the scope of the present system and structures, which, as a matter of language, might be said to fall therebetween.

The invention claimed is:

1. A pressure assist system for facilitating vascular hemostasis, comprising:
    a support bar;
    a midbar extending perpendicularly from a middle portion of the support bar, for supporting a user's thumb when the user grasps the midbar;
    a base extending perpendicularly from a bottom of the support bar, for supporting the user's knuckles when the user grasps the midbar,
    a foot configured with a bottom surface of the base, for pressing against a wound, and wherein the foot is removably attached to the bottom surface of the base.

2. The system of claim 1, the midbar comprising a removable midbar configured with a peg for removably attaching to the support bar at one or more support bar holes.

3. The system of claim 2, the one or more support bar holes comprising a plurality of support bar holes disposed along the support bar, wherein a position of the midbar is adjustable via the support bar holes, to accommodate a range of user hand sizes or gripping positions.

4. The system of claim 1, further comprising a brace configured with the support bar and above the midbar, for facilitating support of a user's wrist or arm when the user grips the midbar and rests the wrist or arm against the support bar.

5. The system f claim 1, the support bar, midbar and base formed as a unitary body.

6. The system of claim 1, wherein the midbar, the base and the foot are aligned within a vertical plane when a bottom surface of the foot rests on a horizontal surface.

7. The system of claim 1, wherein the midbar is offset from the base and the foot such that a vertical plane intersecting the midbar is parallel to a vertical plane intersecting the support bar, the base and the foot when a bottom surface of the foot rests on a horizontal surface.

8. The system of claim 7, wherein the offset is adjustable, to accommodate a range of gripping positions.

9. The system of claim 1, wherein the foot comprises one or both of a fastener and an adhesive, for attaching the foot to the bottom surface of the base.

10. The system of claim 1, wherein part or all of the system is disposable.

11. A pressure assist system for a facilitating vascular hemostasis, comprising:
- a support bar for supporting a user's arm or wrist;
- an adjustable midbar for supporting a user's thumb when the user grips the midbar using the thumb, the midbar extending perpendicularly from the support bar when connected with the support bar at one of a plurality of user-selectable connection points;
- a base formed with a bottom of the support bar and extending perpendicularly from the support bar, for supporting the user's knuckles when the user grips the midbar with the thumb;
- a foot connected with a bottom surface of the base, pressing against a wound, and wherein the foot is removably attached to the bottom surface of the base.

12. The system of claim 11, the connection points comprising holes arranged vertically and horizontally along the support bar, the midbar comprising at least one peg configured to mate with the holes to adjust a position of the midbar to accommodate a range of user grips.

13. The system of claim 11, further comprising a disposable covering to protect at least the foot.

14. A pressure assist system for facilitating manual hemostasis of a wound, comprising a hand-held hemostatic assist device having:
- a vertically-oriented support bar for supporting a medial or lateral surface of a user's wrist;
- a midbar for supporting a user's hand when the user grips the midbar, the midbar connecting with the support bar at one of a plurality of user-selectable connection points, wherein the midbar extends horizontally from the support bar when connected;
- a horizontally-oriented base extending from a bottom portion of the support bar, for transferring pressure applied by the user from the hemostatic assist device to the wound and wherein a disposable foot removably attaches to a bottom surface of the base via a fastener disposed with the foot or the base.

15. The system of claim 14, the base configured for supporting a user's knuckles when the user grips the midbar using at least a thumb.

16. The system of claim 14, the support bar and the base comprising a unitary body; the midbar having a peg for selectively securing with the connection points according to user grip preference.

17. The system of claim 14, further comprising a peg comprising a screw or lock-and-key features, for mating with the connection points.

18. A method for facilitating vascular hemostasis, comprising:
- providing a hand-held pressure assist system, the system having:
  - a support bar, a midbar extending perpendicularly from a center portion of the support bar,
  - a base extending perpendicularly from a bottom of the support bar, and
  - a foot removably attached to a bottom surface of the base;
- positioning a thumb over the midbar and at least one knuckle on the base;
- positioning the system over a wound such that the foot covers the wound; and
- applying downward pressure to the midbar and the base with the thumb and at least one knuckle, until hemostasis is achieved.

19. The method of claim 18, further comprising adjusting the midbar up or down the support bar, to accommodate a user's hand size.

20. A pressure assist system for facilitating vascular hemostasis, comprising:
- an adjustable midbar;
- a support bar for supporting a user's arm or wrist along a medial or lateral surface the support bar having a plurality of connection points for accepting the adjustable midbar;
- a base extending perpendicularly from a bottom portion of the support bar, for transferring pressure from a user's knuckles to a wound, the base supporting the user's knuckles when the medial or lateral arm or wrist surface contacts the support bar; and
- a disposable foot for removably attaching with the base and for contacting the wound.

* * * * *